US009635999B2

(12) United States Patent
Fujitani et al.

(10) Patent No.: US 9,635,999 B2

(45) Date of Patent: May 2, 2017

(54) ENDOSCOPE

(71) Applicant: OLYMPUS CORPORATION, Tokyo (JP)

(72) Inventors: Kiwamu Fujitani, Hachioji (JP); Keigo Takeshima, Hachioji (JP); Motohiro Kuroda, Hachioji (JP); Yasuo Takeuchi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 202 days.

(21) Appl. No.: 14/581,035

(22) Filed: Dec. 23, 2014

(65) Prior Publication Data

US 2015/0112139 A1 Apr. 23, 2015

Related U.S. Application Data

(63) Continuation of application No. PCT/JP2013/083889, filed on Dec. 18, 2013.

(30) Foreign Application Priority Data

Dec. 26, 2012 (JP) ................................ 2012-283230

(51) Int. Cl.

*A61B 1/00* (2006.01)
*A61B 1/04* (2006.01)

(Continued)

(52) U.S. Cl.

CPC ........ *A61B 1/00066* (2013.01); *A61B 1/0052* (2013.01); *A61B 1/00071* (2013.01); *G02B 23/2476* (2013.01)

(58) Field of Classification Search

CPC ... A61B 1/00; A61B 1/00064; A61B 1/00066; A61B 1/012; A61B 1/018; A61B 1/005;

(Continued)

(56) References Cited

U.S. PATENT DOCUMENTS 4,989,581 A 2/1991 Tamburrino et al.
5,469,852 A * 11/1995 Nakamura .............. A61B 8/12 600/463

(Continued)

FOREIGN PATENT DOCUMENTS

JP 62-275425 A 11/1987
JP 07-000345 A 1/1995

(Continued)

OTHER PUBLICATIONS

Extended Supplementary European Search Report dated Feb. 1, 2016 from related European Application No. 13 86 9321.3.

(Continued)

*Primary Examiner* — Anhtuan T Nguyen
*Assistant Examiner* — William Chou
(74) *Attorney, Agent, or Firm* — Scully, Scott, Murphy & Presser, P.C.

(57) ABSTRACT

An endoscope including an operation portion, an insertion portion pivotable relative to the operation portion, and a rotation knob to pivot the insertion portion about an axis of the insertion portion, includes: an insertion portion neutral position indicating portion, provided on an outer circumferential face of the rotation knob, configured to indicate a neutral position; and an indication ring, provided at the operation portion configured to include an operation portion neutral position indicating portion linearly aligned with the insertion portion neutral position indicating portion in an axis direction and indicating that the insertion portion is positioned at a neutral position, and two rotational angle indicating portions provided so as to be apart from the operation portion neutral position indicating portion in a circumferential direction, each of the two rotational angle indicating portions indicating rotation of the insertion portion.

7 Claims, 5 Drawing Sheets

(51) Int. Cl.
*A61B 1/06* (2006.01)
*G02B 23/24* (2006.01)
*A61B 1/005* (2006.01)

(58) Field of Classification Search
CPC ....... A61B 1/0051; A61B 1/0052; A61B 1/01; A61B 1/0125; A61B 90/00; A61B 90/36; A61B 90/361; A61B 2090/701
USPC ........ 600/103, 114, 117, 118, 125, 137, 145, 600/146, 160; 606/108
See application file for complete search history.

(56) References Cited

U.S. PATENT DOCUMENTS 5,601,601 A * 2/1997 Tal ......................... A61B 17/29 606/174
2005/0125002 A1* 6/2005 Baran ............... A61M 25/0041 606/108
2007/0212913 A1 9/2007 Takeuchi et al.

FOREIGN PATENT DOCUMENTS

JP H07-032758 B2 4/1995
JP 2004-305413 A 11/2004
JP 2005-124632 A 5/2005
JP 2009-050540 A 3/2009
JP 2010-234058 A 10/2010

OTHER PUBLICATIONS

International Search Report dated Jan. 28, 2014 issued in PCT/JP2013/083889.

* cited by examiner 2
1a
7
12
36
52
3M2
3H
64
69
Y5
Y5
30
30h
31
35
34
32
51
24
Y4
Y4
65
63
3R
68
23
20
21
62
3C
61
3M1

ENDOSCOPE

CROSS REFERENCE TO RELATED APPLICATION

This application is a continuation application of PCT/JP2013/083889 filed on Dec. 18, 2013 and claims benefit of Japanese Application No. 2012-283230 filed in Japan on Dec. 26, 2012, the entire contents of which are incorporated herein by this reference.

BACKGROUND OF INVENTION

1. Field of the Invention

The present invention relates to an endoscope that allows an operation to rotate an insertion portion relative to an operation portion.

2. Description of the Related Art

Endoscopes each include an elongated flexible insertion portion. The endoscopes are used in, e.g., medical and industrial fields. The insertion portion includes a distal end portion, a bending portion and a flexible tube portion having flexibility in this order from the distal end side. At a proximal end portion of the insertion portion, an operation portion, which is held and operated by an operator, is disposed.

The elongated insertion portion may be inserted to a lumen including a plurality of branch portions such as a bronchus. In this case, a surgeon repeatedly performs, e.g., an operation to bend the bending portion and an operation to twist the operation portion and the insertion portion to insert the insertion portion to a deep part of the lumen.

Japanese Patent Application Laid-Open Publication No. 2010-234058 discloses an endoscope that allows an operation to rotate an insertion portion relative to an insertion portion. With the endoscope, for example, when a surgeon performs an operation to rotate the insertion portion relative to the operation portion, the amount of strength required for the rotation increases as a rotational position of the insertion portion moves away from a neutral position.

Accordingly, the surgeon can grasp the rotational position relative to the neutral position, from the change in the amount of strength.

In the case of the endoscope disclosed in Japanese Patent Application Laid-Open Publication No. 2010-234058, when the insertion portion is inserted to a bronchus, a surgeon performs an operation to rotate the insertion portion relative to the operation portion instead of performing a twisting operation to twist the operation portion and the insertion portion, while observing an endoscopic image displayed on a screen of a monitor.

Then, when the surgeon inserts a distal end portion of the insertion portion to, for example, a main bronchus, confirms on the endoscopic image that the insertion portion has rotated by 90 degrees, and then makes the bending portion bend, for example, upward to insert the distal end portion of the insertion portion to the main bronchus. Subsequently, the surgeon repeatedly performs an operation to properly rotate the insertion portion relative to the operation portion and an operation to properly bend the bending portion to insert the distal end portion of the insertion portion to a target site.

With this configuration, making the insertion portion rotate relative to the operation portion instead of the twisting operation enhances the operability and reduces a period of time required for the procedure, resulting in substantial reduction in burden on a surgeon and a patient.

SUMMARY OF THE INVENTION

An endoscope according to an aspect of the present invention includes an operation portion, an insertion portion provided so as to be pivotable relative to the operation portion, a rotation knob to be operated when the insertion portion is made to pivot about an axis of the insertion portion relative to the operation portion, an insertion portion neutral position indicating portion, provided on an outer circumferential face of the rotation knob, configured to indicate a neutral position in a direction in which the insertion portion pivots; and an indication ring provided at the operation portion, the indication ring configured to include an operation portion neutral position indicating portion aligned with the insertion portion neutral position indicating portion in an endoscope rotation axis direction and indicating that the insertion portion is positioned at a neutral position, and two rotational angle indicating portions each provided so as to be apart from the operation portion neutral position indicating portion in a circumferential direction at the same angle, each of the two rotational angle indicating portions indicating rotation of the insertion portion around the axis by a predetermined angle.

DETAILED DESCRIPTION OF THE PREFERRED EMBODIMENT(S)

An embodiment of the present invention will be described with reference to the drawings.

Figure 1:
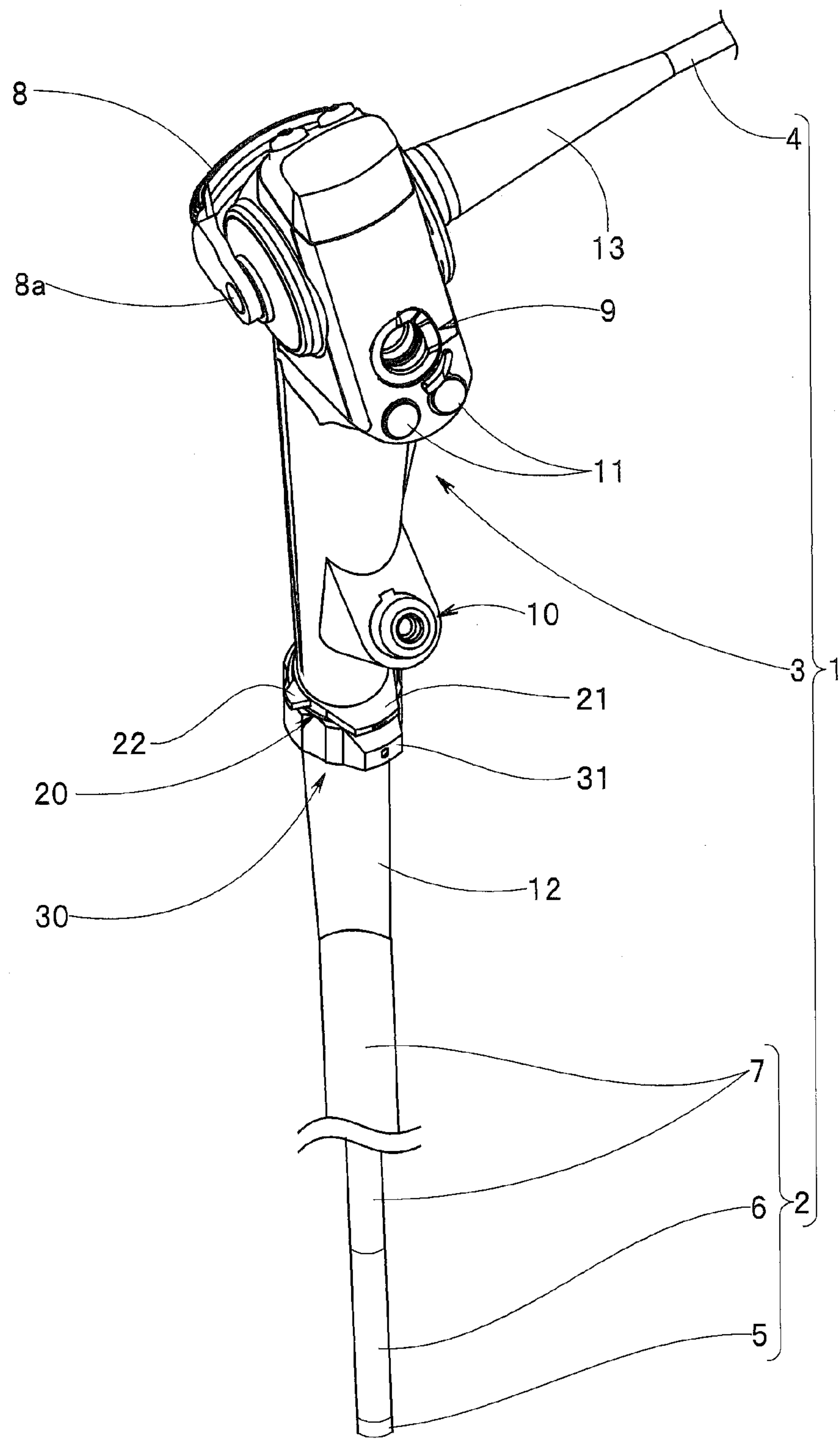
FIG. 1 is a diagram illustrating an endoscope including a rotation knob at an operation portion thereof.

As illustrated in FIG. 1, the endoscope 1 includes an insertion portion 2, an operation portion 3 and a universal cord 4.

The insertion portion 2 includes a distal end rigid portion 5, a bending portion 6 and a flexible tube portion 7, which are continuously provided in this order from the distal end side. The bending portion 6 is configured to be bendable in, for example, two directions. The flexible tube portion 7 is configured to be long and flexible.

The operation portion 3 is provided at a proximal end portion of the insertion portion 2. In the operation portion 3, a bending lever 8, an air/water feeding cylinder 9, a treatment instrument insertion port 10 and various switches 11 are provided. In the operation portion 3, an indication ring 20 and a rotation knob 30, which will be described later, are provided.

The switches 11 include, e.g., a switch for generating a freeze signal or a switch for generating a release signal. The treatment instrument insertion port 10 allows a non-illustrated endoscopic treatment instrument such as biopsy forceps to be inserted therethrough. At the air/water feeding cylinder 9, a non-illustrated suction button is arranged. The bending lever 8 is an operation apparatus for bending the bending portion 6 upward or downward. The bending lever 8 is pivotable about a knob shaft 8*a*.

The rotation knob 30 is provided at a connection part between the insertion portion 2 and the operation portion 3 in such a manner that the rotation knob 30 is rotatable around a longitudinal axis. The rotation knob 30 includes an insertion portion neutral position indicating portion 31. The indication ring 20 is fixedly provided in the vicinity of the rotation knob 30. The indication ring 20 includes an operation portion neutral position indicating portion 21 and a pair of rotational angle indicating portions 22.

Note that reference numeral 12 denotes a first bend preventing member. The first bend preventing member 12 covers the proximal end portion of the insertion portion 2 and thereby prevents the proximal end portion from being buckled. Reference numeral 13 denotes a second bend preventing member. The second bend preventing member 13 covers a distal end portion of the universal cord 4 and thereby prevents the distal end portion from being buckled.

Here, a configuration of the connection part between the insertion portion 2 and the operation portion 3, at which the rotation knob 30 is provided rotatably, will be described.

Figure 2:
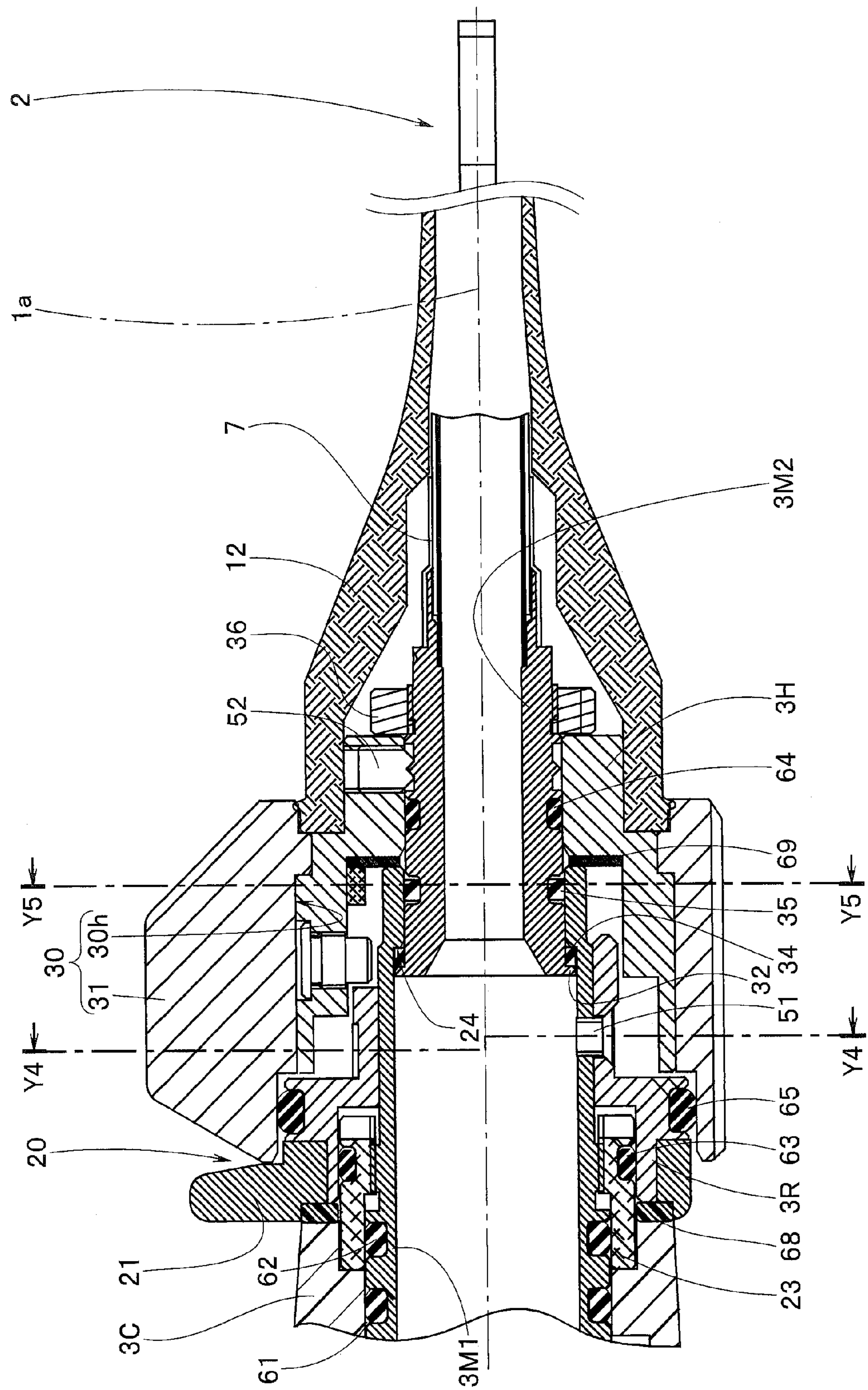
FIG. 2 is a longitudinal cross-sectional view illustrating a configuration of a connection part between the operation portion including the rotation knob and an insertion portion.

As illustrated in FIG. 2, the operation portion 3 mainly includes an operation portion case body 3C, an operation portion-side fixed ferrule 3M1, an indication ring fixing member 3R, a pivoting operation portion housing (hereinafter abbreviated as "housing") 3H and an insertion portion-side fixed ferrule 3M2.

The operation portion case body 3C is an operation portion body and has a cylindrical shape. Each of the operation portion-side fixed ferrule 3M1, the housing 3H and the insertion portion-side fixed ferrule 3M2 has a pipe shape. The indication ring fixing member 3R has a ring shape.

The indication ring 20 is integrally attached to the indication ring fixing member 3R. On the other hand, the rotation knob 30 is integrally attached to the housing 3H.

Figure 3:
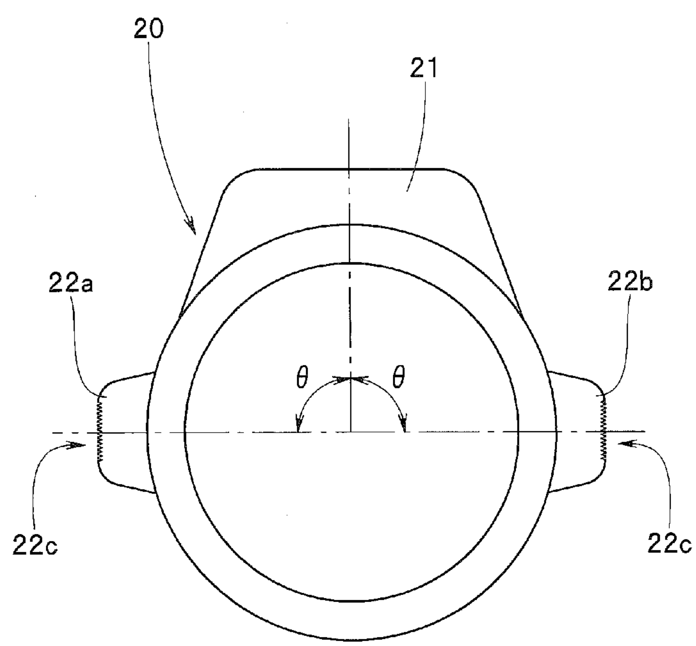
FIG. 3 is a diagram illustrating an indication ring.

As illustrated in FIG. 3, the indication ring 20 is a ring-shaped member. The indication ring 20 includes the operation portion neutral position indicating portion 21 and the pair of rotational angle indicating portions 22*a* and 22*b* at respective predetermined positions. The operation portion neutral position indicating portion 21 is a projection portion that protrudes from an outer circumferential face of the indication ring 20 and is formed in a predetermined outer shape. Each of the pair of indicating portions 22*a* and 22*b* is a projection portion that protrudes from the outer circumferential face of the indication ring 20, and is formed in a predetermined outer shape. Each of the first rotational angle indicating portion 22*a* and the second rotational angle indicating portion 22*b* are each provided on either side of the operation portion neutral position indicating portion 21 at an angle θ in a circumferential direction.

A top face of each of the pair of rotational angle indicating portions 22*a* and 22*b* provides an identification portion 22*c*. In each of the top faces, which provides an identification portion 22*c*, for example, a plurality of recess and projection portions are provided. This configuration enables a surgeon to identify a positional relationship between the operation portion neutral position indicating portion 21 and the first rotational angle indicating portion 22*a* or a positional relationship between the operation portion neutral position indicating portion 21 and the second rotational angle indicating portion 22*b* with his/her finger tips without reliance on visual confirmation.

In the present embodiment, the angle θ is set to 90 degrees which is a request of a surgeon, in order to indicate that the insertion portion 2 has been rotated around an axis by 90 degrees relative to the operation portion 3.

Note that in the above description, the operation portion neutral position indicating portion 21 and the pair of rotational angle indicating portions 22*a* and 22*b* are provided in the indication ring 20, which is a ring-shaped member. However, the operation portion neutral position indicating portion 21, the first rotational angle indicating portion 22*a* and the second rotational angle indicating portion 22*b* may be formed by respective independent members, and each of the independent members may be fixedly provided at the operation portion. In this case, different materials are used for the operation portion neutral position indicating portion 21, the first rotational angle indicating portion 22*a* and the second rotational angle indicating portion 22*b* to enable discrimination among the operation portion neutral position indicating portion 21, the first rotational angle indicating portion 22*a* and the second rotational angle indicating portion 22*b*.

As illustrated in FIG. 2, the operation portion case body 3C and the indication ring fixing member 3R are integrated with the operation portion-side fixed ferrule 3M1.

At an inner circumferential face of a joining member 23, a female thread is formed. A male thread of the operation portion-side fixed ferrule 3M1 is screwed with the female thread of the joining member 23.

Figure 4:
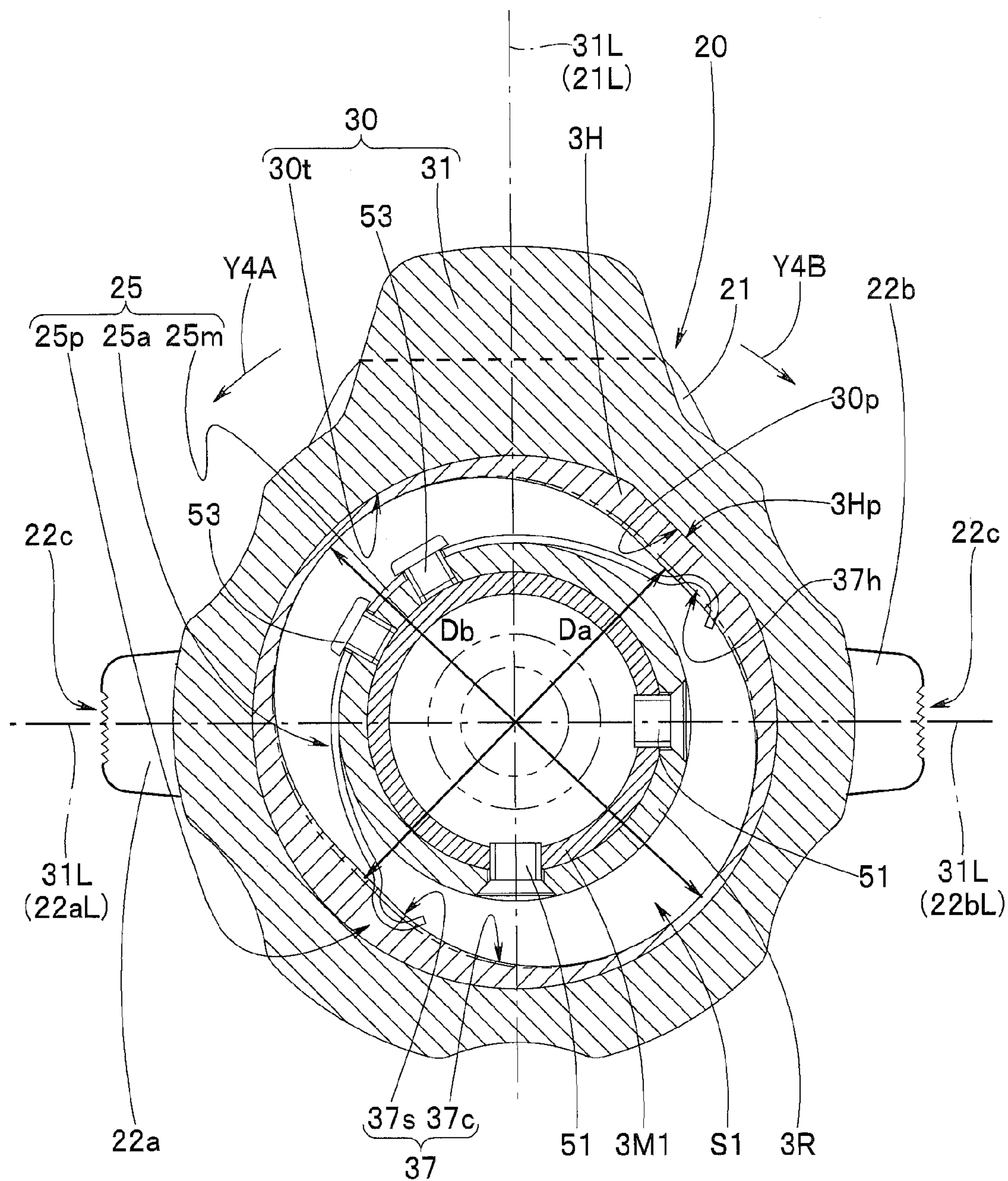
FIG. 4 is a cross-sectional view along line Y4-Y4 in FIG. 2.

The operation portion-side fixed ferrule 3M1 is arranged inside the operation portion case body 3C. An end portion of the operation portion-side fixed ferrule 3M1 protrudes from an end face of the joining member 23. As illustrated in FIGS. 2 and 4, the indication ring fixing member 3R with the indication ring 20 arranged on a stepped part thereof is fastened and thereby fixed to a predetermined position on the end portion of the operation portion-side fixed ferrule 3M1 by first screw members 51.

Reference numeral 61 denotes a first O-shaped ring. The first O-shaped ring 61 ensures water tightness between the operation portion case body 3C and the operation portion-side fixed ferrule 3M1.

Reference numeral 62 denotes a second O-shaped ring. The second O-shaped ring 62 ensures water tightness between the operation portion-side fixed ferrule 3M1 and the joining member 23.

Reference numeral 63 denotes a third O-shaped ring. The third O-shaped ring 63 ensures water tightness between the joining member 23 and the indication ring fixing member 3R.

Reference numeral 68 denotes a first annular elastic member. The first annular elastic member 68 elastically holds the indication ring 20, whereby the state of the indication ring 20 sandwiched between the operation portion case body 3C and the indication ring fixing member 3R is stably held.

On the other hand, the housing 3H, which is integrated with the rotation knob 30, and the insertion portion 2 are integrated with the insertion portion-side fixed ferrule 3M2.

Figure 5:
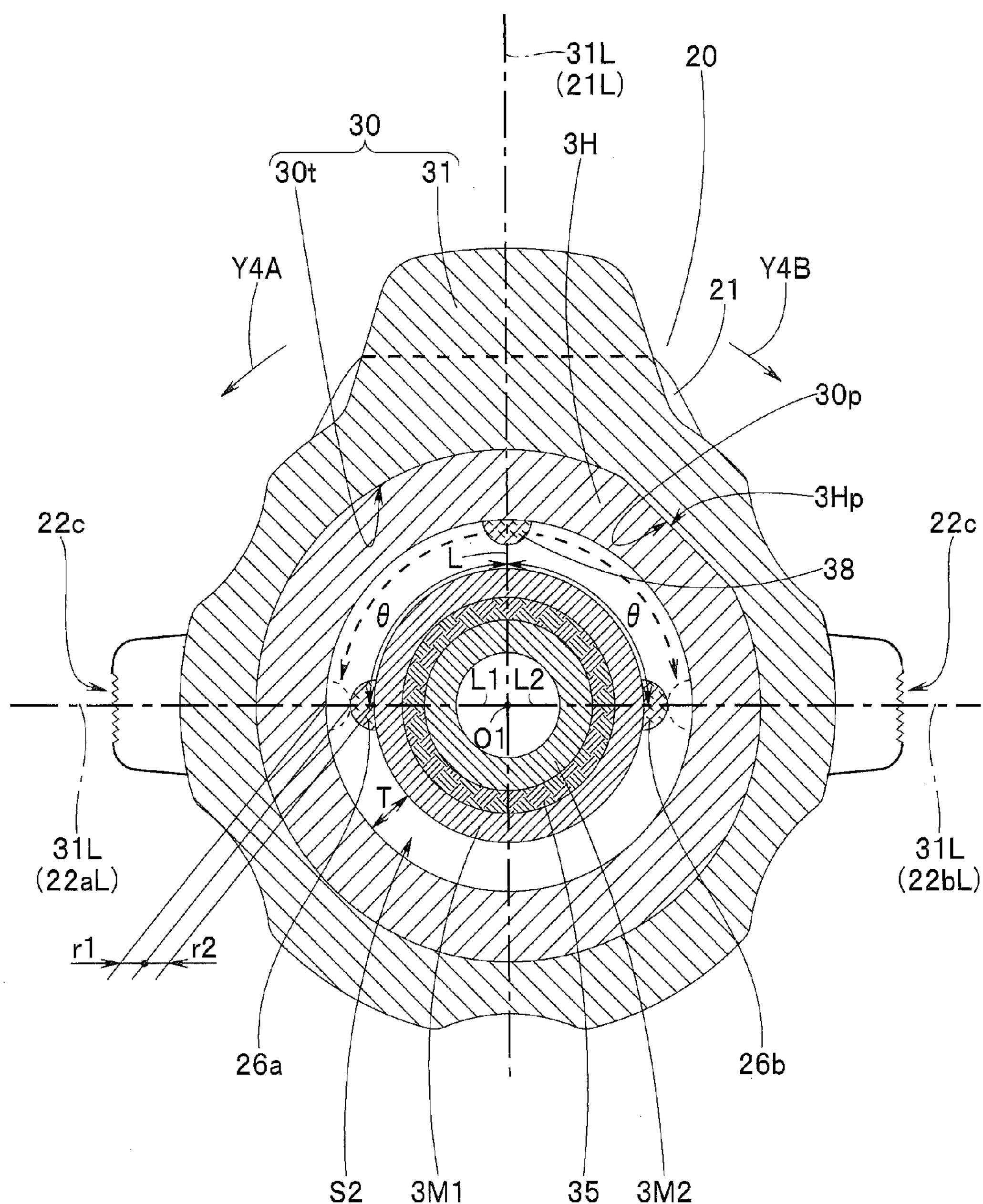
FIG. 5 is a cross-sectional view along line Y5-Y5 in FIG. 2.

As illustrated in FIGS. 2, 4 and 5, the rotation knob 30 is integrally fixed to the housing 3H. The rotation knob 30 is an annular member. The rotation knob 30 includes the insertion portion neutral position indicating portion 31 and a housing arrangement hole 30*t*.

The insertion portion neutral position indicating portion 31 is a projection portion that protrudes from a predetermined outer circumferential face of the rotation knob 30, and is formed in a predetermined outer shape. The housing arrangement hole 30*t* is a through hole for arranging the housing 3H therein. The housing arrangement hole 30*t* is formed substantially in a D-shape. The housing arrangement hole 30*t* includes a turn preventing flat face 30*p*.

The housing 3H is a cylindrical body. The housing 3H is formed substantially in a D-shape as with the housing arrangement hole 30*t*. In other words, the housing 3H includes a flat face 3Hp in an outer circumferential face thereof. The flat face 3Hp is in abutment with the turn preventing flat face 30*p*.

In this configuration, arranging the housing 3H in the housing arrangement hole 30*t* of the rotation knob 30 prevents rotation of the rotation knob 30 relative to the housing 3H.

The rotation knob 30 and the housing 3H are integrally fixed to each other by, e.g., bonding or screwing the rotation knob 30 and the housing 3H together.

The housing 3H, which is integrated with the rotation knob 30, is integrally fastened and thereby fixed at a predetermined position in a longitudinal axis direction of the insertion portion-side fixed ferrule 3M2 by second screw members 52. Also, an end portion of the flexible tube portion 7 included in the insertion portion 2 is integrally fixed to the insertion portion-side fixed ferrule 3M2.

Reference numeral 64 denotes a fourth O-shaped ring. The fourth O-shaped ring 64 ensures water tightness between the housing 3H and the insertion portion-side fixed ferrule 3M2.

The insertion portion-side fixed ferrule 3M2 is pivotally arranged in a through hole of the operation portion-side fixed ferrule 3M1. A center axis of the insertion portion-side fixed ferrule 3M2 and a center axis of the operation portion-side fixed ferrule 3M1 coincide with each other, and both coincide with an endoscope rotation axis 1*a*.

A flange 32 is provided at an end portion of the insertion portion-side fixed ferrule 3M2. A step 24 is provided in an inner circumferential face of the end portion of the operation portion-side fixed ferrule 3M1. As a result of the flange 32 being caught by the step 24, the insertion portion-side fixed ferrule 3M2 is prevented from coming off from the operation portion-side fixed ferrule 3M1.

The flange 32 and the step 24 are held in abutment with each other via, for example, a first washer-shaped member 34 that enhances the slippage, the first washer-shaped member 34 including, for example, a resin. Reference numeral 35 denotes a second washer-shaped member, which is fixedly provided at a predetermined position on the insertion portion-side fixed ferrule 3M2.

The insertion portion-side fixed ferrule 3M2 rotates smoothly as a result of the flange 32 and the step 24 being brought into abutment with each other via the first washer-shaped member 35 and an outer circumferential face of the second washer-shaped member 35 and an inner circumferential face of the operation portion-side fixed ferrule 3M1 being brought into abutment with each other.

Reference numeral 36 denotes a fixing adjustment ring. The fixing adjustment ring 36 is arranged so as to be screwed with a male thread portion formed at an outer circumference of the insertion portion-side fixed ferrule 3M2. The fixing adjustment ring 36 allows fine adjustment of a fastening state to set the abutment between the flange 32 of the insertion portion-side fixed ferrule 3M2 and the step 24 of the operation portion-side fixed ferrule 3M1 into an optimum state.

Reference numeral 65 denotes a fifth O-shaped ring. The fifth O-shaped ring 65 ensures water tightness between the rotation knob 30 and the indication ring fixing member 3R.

Reference numeral 69 denotes a second annular elastic member. The second annular elastic member 69 is arranged in a compressed state between the operation portion-side fixed ferrule 3M1 and the housing 3H. The second annular elastic member 69 holds a fastening state of the fixing adjustment ring 36 in a predetermined state so that the housing 3H, which is repeatedly made to pivot relative to the operation portion-side fixed ferrule 3M1, consistently stably rotates.

With the above-described configuration, upon the rotation knob 30 being rotated, the insertion portion-side fixed ferrule 3M2 with the housing 3H and the insertion portion 2 integrated thereto rotates relative to the operation portion-side fixed ferrule 3M1 with the operation portion case body 3C, the indication ring fixing member 3R and the indication ring 20 integrated thereto.

Here, a neutral position, which is a reference position for rotation of the insertion portion 2 that rotates relative to the operation portion 3, will be described.

Here, the side of the operation portion 3 on which the bending lever 8 is disposed is the front side and the side opposite to the front side is the back side. It is assumed that when the insertion portion 2 is in a straightened state, if the bending lever 8 is operated from the distal end side toward the proximal end side of the insertion portion 2 to bend the bending portion 6 from the back side toward the front side in parallel with the direction of the rotation of the bending lever 8, the insertion portion 2 is at a neutral position relative to the operation portion 3.

As illustrated in FIGS. 4 and 5, when the insertion portion 2 is positioned at the neutral position at which the insertion portion 2 is not rotated relative to the operation portion 3, there is a positional relationship in which a center line 31L of the insertion portion neutral position indicating portion 31 and a center line 21L of the operation portion neutral position indicating portion 21 overlap each other. In other words, when the insertion portion 2 is positioned at the neutral position, the insertion portion neutral position indicating portion 31 and the operation portion neutral position indicating portion 21 are linearly aligned in an axis direction of the endoscope rotation axis 1*a*. This positional relationship is referred to as "insertion portion initial position" (hereinafter abbreviated as "initial position").

At the initial position, the rotation knob 30 is operated to rotate in the arrow Y4A direction in FIG. 4 by 90 degrees relative to the operation portion 3, whereby the insertion portion 2 also rotates around the axis by 90 degrees relative to the operation portion 3.

Here, the insertion portion neutral position indicating portion 31 provided at the rotation knob 30 also rotates by 90 degrees. As a result, a positional relationship in which the center line 31L of the insertion portion neutral position indicating portion 31 and a center line 22*a*L of the rotational angle indicating portion 22*a* overlap each other is provided.

On the other hand, at the initial position, if the rotation knob 30 is operated to rotate in the arrow Y4B direction, which is the opposite direction, the insertion portion 2 rotates in that opposite direction relative to the operation portion 3. Then, the insertion portion neutral position indicating portion 31 provided at the rotation knob 30 rotates by 90 degrees, whereby a positional relationship in which the center line 31L of the insertion portion neutral position indicating portion 31 and a center line 22*b*L of the rotational angle indicating portion 22*b* overlap each other is provided.

The above-described insertion portion 2 is configured to rotate by the same angle in both rotation directions, which are the arrow Y4A direction and the arrow Y4B direction, from the initial position indicated in FIG. 4. In the present embodiment, the insertion portion 2 is configured to rotate, for example, by 120 degrees in each of the arrow Y4A direction and the arrow Y4B direction in consideration of the operability.

As illustrated in FIG. 4, a first space S1 having a predetermined shape is formed between a round-shape outer circumferential face of the indication ring fixing member 3R and an odd-shape inner circumferential face of the housing 3H. Note that the odd shape, here, refers to a shape other than a round shape.

A leaf spring 25 is fixedly provided on an outer circumferential face of the indication ring fixing member 3R. More specifically, the leaf spring 25 is fixed via, for example, screw members 53 with an attachment portion 25*m* arranged in a circumferential positioning groove (not illustrated) formed at a predetermined position in the outer circumferential face of the indication ring fixing member 3R.

The leaf spring 25 has a predetermined elastic force when the leaf spring 25 is in a predetermined shape. The leaf spring 25 includes the attachment portion 25*m* and a pair of arm portions 25*a*. The arm portions 25*a* are provided on the opposite sides across the attachment portion 25*m*. At an end portion of each of the arm portions 25*a*, a sliding protrusion 25*p* whose outer surface has a curved shape is provided. The leaf spring 25 has a shape that is symmetrical with respect to a center portion of the attachment portion 25*m*.

The inner circumferential face of the housing 3H provides an abutment surface 37 to which each sliding protrusion 25*p* abuts. The inner circumferential face of the housing 3H is shaped so that the amount of strength required for rotating the insertion portion 2 varies along with rotation of the insertion portion 2 according to a rotational position of the insertion portion 2 relative to the operation portion 3.

The abutment surface 37 has, for example, a long hole shape including two curved portions 37*c* and two straight portions 37*s*. A first diameter portion Da, which corresponds to a distance between the straight portions 37*s*, is set to be shorter than a second diameter portion Db, which corresponds to a distance between the curved portions 37*c*, by a predetermined amount.

When the insertion portion 2 is positioned at the initial position, the sliding protrusions 25*p* of the leaf spring 25 are arranged so as to be biased against the straight portions 37*s* of the abutment surface 37 by biasing forces of the arm portions 25*a*.

Also, depressions 37*h* are formed on respective predetermined positions in the straight portions 37*s*. When the insertion portion 2 is positioned at the initial position, end portions of the sliding protrusions 25*p* are arranged so as to engage with the respective depressions 37*h*.

The depressions 37*h* are set to have a diameter dimension and a depth dimension that allow the end portions of the sliding protrusions 25*p* to be depressed by a predetermined amount.

Note that in the above description, the abutment surface 37 has a long hole shape. However, the shape of the abutment surface 37 is not limited to the long hole shape and may be, e.g., a triangular shape with an apex portion formed to be gentle or an oval shape as long as such shape at least includes a first diameter portion Da and a second diameter portion Db that have respective diameters that are different from each other and does not hinder movement of the sliding protrusions 25*p*.

As illustrated in FIG. 5, a second space S2 having a predetermined shape is formed between a round outer circumferential face of the operation portion-side fixed ferrule 3M1 and a round inner circumferential face of the housing 3H.

On the inner circumferential face of the housing 3H, one rotary projection portion 38, which is included in a rotation angle indicating portion, is provided. On the other hand, on the outer circumferential face of the operation portion-side fixed ferrule 3M1, two angle indicating projection portions 26*a* and 26*b* are provided. The rotary projection portion 38 is formed in, for example, a semicircular shape using a rigid member. On the other hand, the angle indicating projection portions 26*a* and 26*b* are each formed in, for example, a semicircular shape using an elastic member.

A position of the rotary projection portion 38 and positions of the rotational angle indicating portions 22*a* and 22*b* are set as follows.

An angle θ formed by a first line segment L1 connecting a center of the first angle indicating projection portion 26*a* and a center O1 on the endoscope rotation axis 1*a* and a center line segment L connecting a center of the rotary projection portion 38 and the center O1 is set to 90 degrees, and an angle θ formed by a second line segment L2 connecting a center of the second angle indicating projection portion 26*b* and the center O1, and the center line segment L is set to 90 degrees. In other words, the center of the rotary projection portion 38 is positioned on the center line segment L, which is a bisector of an angle formed by the first line segment L1 and the second line segment L2.

In the present embodiment, when the insertion portion 2 is at the initial position, the rotary projection portion 38 is provided on an extension of the center line of the insertion portion neutral position indicating portion 31, and the angle indicating projection portions 26*a* and 26*b* are each provided on an extension of the center lines of the rotational angle indicating portions 22*a* and 22*b*.

Also, the following relationship is set among a gap T in the second space S2, a radius r1 of the rotary projection portion 38 and respective radiuses r2 of the angle indicating projection portions 26*a* and 26*b*:

$$T<r1+r2.$$

Note that in the above description, the rotary projection portion 38 includes a rigid member, and the angle indicating projection portions 26*a* and 26*b* each include an elastic member. However, the rotary projection portion 38 and the angle indicating projection portions 26*a* and 26*b* each may include an elastic member. Also, it is possible that the rotary projection portion 38 includes an elastic member and the angle indicating projection portions 26*a* and 26*b* each include a rigid member.

Also, in the above description, the rotary projection portion 38 and the angle indicating projection portions 26*a* and 26*b* each have a semicircular shape. However, the shape of each of the rotary projection portion 38 and the angle indicating projection portions 26*a* and 26*b* are not limited to a semicircular shape and may be, e.g., a rectangular shape such as a quadrangular shape or a trapezoidal shape or a shape including a curved surface. In other words, it is only necessary that the following relationship be set among a height h1 of the rotary projection portion 38, heights h2 of the angle indicating projection portions 26*a* and 26*b* and the gap T:

$$T<h1+h2.$$

Furthermore, the rotary projection portion 38 and the angle indicating projection portions 26*a* and 26*b* are provided at respective positions that are different from a position of the leaf spring 25 in the axial direction in consideration of ease of assembly.

An operation of the endoscope 1 configured as described above will be described.

When an examination of a bronchus is conducted, the endoscope 1 is prepared. Then, whether or not the operation portion neutral position indicating portion 21 and the insertion portion neutral position indicating portion 31 coincide with each other is confirmed.

A doctor grasps the endoscope 1 and confirms that the insertion portion 2 is positioned at the initial position. Subsequently, the doctor inserts the insertion portion 2 while observing an endoscopic image displayed on a screen of a monitor. Then, the doctor confirms from the endoscopic image that the insertion portion 2 has reached a branch of a trachea and then rotates the rotation knob 30 in a desired direction to rotate the insertion portion 2 relative to the operation portion 3.

When the insertion portion 2 is positioned in the initial position, upon a start of an operation to rotate the rotation knob 30, the amount of strength of the rotation start operation is large because the sliding protrusions 25*p* of the leaf spring 25 engage with the respective depressions 37*h*. Then, upon disengagement between the sliding protrusions 25*p* and the depressions 37*h*, a sense of a click is given and the insertion portion 2 starts rotating. Then, as the rotation knob 30 is moved away from the initial position, the amount of strength required for the rotation decreases and the insertion portion 2 rotates smoothly.

If the doctor continues the rotation operation, his/her finger that is operating the rotation knob 30 comes into contact with the rotational angle indicating portion 22*a* and the doctor thereby can recognize that the amount of the rotation is close to 90 degrees. Here, the doctor further continues the rotation operation. Then, the rotary projection portion 38 abuts to the angle indicating projection portion 26*a*, and subsequently, the amount of strength for operating the rotation knob 30 to rotate increases. Consequently, the doctor can grasp that the rotation knob 30 has been rotated by 90 degrees.

Here, the surgeon, while observing the endoscopic image, performs an operation to properly bend the bending portion 6 to insert the insertion portion 2 to the inside of a target main bronchus. Subsequently, the surgeon, while observing the endoscopic image, performs an operation to properly bend the bending portion 6 to insert the insertion portion 2 toward a target site.

Note that if the doctor performs a rotation operation to return the insertion portion 2 to the initial position, a sense of a click is given to the doctor as a result of the sliding protrusions 25*p* engaging with the depressions 37*h*, which is the opposite to the above, whereby the doctor can grasp that the insertion portion 2 has reached the initial position.

As described above, the configuration in which the sliding protrusions 25*p* of the leaf spring 25 engage with the depressions 37*h* and provision of the operation portion neutral position indicating portion 21 and the insertion portion neutral position indicating portion 31 at the respective predetermined positions enable the initial position to be reliably confirmed sensuously and visually.

Also, the rotation angle indicating portion including the rotary projection portion 38 and the angle indicating projection portions 26*a* and 26*b*, which abut to the rotary projection portion 38, is provided in the operation portion 3. As a result, the rotary projection portion 38 abuts to the angle indicating projection portion 26*a* or 26*b* and after the abutment, the amount of operation strength for operating the rotation knob 30 to rotate increases, whereby rotation of the insertion portion 2 by a predetermined amount as a result of the operation to rotate the rotation knob 30 can be grasped by the strength amount variation.

In other words, the doctor who is operating the endoscope 1 can quickly make the insertion portion 2 move and rotate by a predetermined amount without reliance on the endoscopic image or without visually confirming the amount of rotational movement of the insertion portion neutral position indicating portion 31.

Also, the identification portions 22*c* are provided at the respective top surfaces of the rotational angle indicating portions 22*a* and 22*b*. As a result, the doctor who is operating the rotation knob 30 to rotate touches an identification portion 22*c*, and thereby can easily grasp a positional relationship between the insertion portion neutral position indicating portion 31 and the rotational angle indicating portion 22*a* or 22*b* or a positional relationship between the insertion portion neutral position indicating portion 31 and the operation portion neutral position indicating portion 21 during the operation.

Therefore, the doctor who is operating the endoscope 1 can perform the rotational operation of the rotation knob 30 while being conscious of the amount of the rotational operation of the rotation knob 30 reaching 90 degrees before the amount of the rotational operation actually reaches 90 degrees. Thus, for example, if the doctor performs an operation to rotate the insertion portion 2 by 90 degrees or more, the doctor can perform an endoscopic examination while properly switching between an operation to rotate the insertion portion 2 to 90 degrees and an operation for rotation subsequent thereto.

Note that the operation portion neutral position indicating portion 21 and the insertion portion neutral position indicating portion 31 may be colored in respective colors that are different from each other. With such configuration, visually confirming that the operation portion neutral position indicating portion 21 and the insertion portion neutral position indicating portion 31 of the different colors are linearly aligned before the endoscope 1 is used for an examination facilitates determination of whether or not the insertion portion 2 is positioned at the initial position.

Where the operation portion neutral position indicating portion 21 and the insertion portion neutral position indicating portion 31 are colored, the operation portion neutral position indicating portion 21 and the insertion portion neutral position indicating portion 31 are colored in respective colors that are different from a color of the operation portion 3 and a color of the insertion portion 2.

Also, in the above-described embodiment, the angle θ is 90 degrees. However, the angle θ can arbitrarily be set to an angle desired by a surgeon.

Note that the present invention is not limited only to the above-described embodiment and various modifications are possible without departing from the spirit of the invention.

What is claimed is:

1. An endoscope comprising:

an operation portion;

an insertion portion provided so as to be pivotable relative to the operation portion;

a rotation knob to be operated when the insertion portion is made to pivot about an axis of the insertion portion relative to the operation portion;

an insertion portion neutral position indicating portion, provided on an outer circumferential face of the rotation knob, configured to indicate a neutral position in a direction in which the insertion portion pivots;

an indication ring, provided at the operation portion, configured to include an operation portion neutral position indicating portion linearly aligned with the insertion portion neutral position indicating portion in a direction of an endoscope rotation axis and indicating that the insertion portion is positioned at a neutral position, and two rotational angle indicating portions each provided so as to be apart from the operation portion neutral position indicating portion in a circumferential direction at a same angle, each of the two rotational angle indicating portions indicating rotation of the insertion portion around the endoscope rotation axis by a predetermined angle, a leaf spring fixed on a side of an operation portion-side fixed ferrule, the operation portion-side fixed ferrule being integrally fixed to the operation portion, the leaf spring including a sliding protrusion that slides relative to an inner circumferential face of a housing with the rotation knob provided thereon;

angle indicating projection portions protrudingly provided on the side of the operation portion-side fixed ferrule, the angle indicating projection portions being each provided so as to be apart in the circumferential direction at a same angle as with the rotational angle indicating portions; and a rotary projection portion protrudingly provided on a bisector that, where the insertion portion is positioned at the neutral position, bisects an angle formed by a first line segment connecting a center of one of the angle indicating projection portions and a center on the endoscope rotation axis, and a second line segment connecting a center of another of the angle indicating projection portions and the center on the endoscope rotation axis.

2. The endoscope according to claim 1, wherein when the insertion portion neutral position indicating portion and the rotational angle indicating portion coincide with each other, the rotary projection portion and the angle indicating projection portion are brought into a predetermined contact state.

3. The endoscope according to claim 2, wherein if the rotary projection portion includes an elastic member, the angle indicating projection portion includes an elastic member or a rigid member, and if the rotary projection portion includes a rigid member, the angle indicating projection portion includes an elastic member.

4. The endoscope according to claim 1, wherein a depression that allows a sliding protrusion of the leaf spring to engage therewith is provided in an inner circumferential face of the housing; and when the insertion portion neutral position indicating portion and the operation portion neutral position indicating portion are linearly aligned in the endoscope rotation axis direction, the sliding protrusion engages with the depression.

5. The endoscope according to claim 1, wherein the rotary projection portion and the angle indicating projection portions are provided at respective positions away from the leaf spring in an endoscope axis direction.

6. The endoscope according to claim 1, wherein at a top face of the rotational angle indicating portion, a recess/projection portion for discrimination between the operation portion neutral position indicating portion and the rotational angle indicating portion is provided.

7. The endoscope according to claim 1, wherein the operation portion neutral position indicating portion and the insertion portion neutral position indicating portion are colored in respective colors that are different from each other.

* * * * *